United States Patent
Shim et al.

(10) Patent No.: US 8,293,591 B2
(45) Date of Patent: Oct. 23, 2012

(54) FIELD EFFECT TRANSISTOR COMPRISING GOLD LAYER, MICROFLUIDIC DEVICE COMPRISING THE FIELD EFFECT TRANSISTOR, AND METHOD OF DETECTING ANALYTE HAVING THIOL GROUP USING THE FIELD EFFECT TRANSISTOR AND THE MICROFLUIDIC DEVICE

(75) Inventors: Jeo-young Shim, Yongin-si (KR); Kyu-tae Yoo, Yongin-si (KR); Kyu-sang Lee, Yongin-si (KR); Won-seok Chung, Yongin-si (KR); Yeon-ja Cho, Yongin-si (KR); Chang-eun Yoo, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 929 days.

(21) Appl. No.: 11/733,539

(22) Filed: Apr. 10, 2007

(65) Prior Publication Data
US 2007/0235760 A1  Oct. 11, 2007

(30) Foreign Application Priority Data

Apr. 10, 2006 (KR) .................. 10-2006-0032413

(51) Int. Cl.
*H01L 31/00* (2006.01)
(52) U.S. Cl. ........ 438/135; 438/142; 257/213; 257/413; 257/192; 257/903; 257/E29.049; 257/E29.067; 257/E29.237; 257/E29.299; 257/E29.325; 257/E29.346
(58) Field of Classification Search .......... 257/213–413, 257/903, E29.049, E29.067, E29.237, E29.299, 257/E29.325, E29.346, 192, E21.19; 438/142, 438/135
See application file for complete search history.

(56) References Cited

U.S. PATENT DOCUMENTS

| 4,238,757 | A | 12/1980 | Schenck |
| 4,777,019 | A | 10/1988 | Dandekar |
| 5,466,348 | A | 11/1995 | Holm-Kennedy |
| 5,804,049 | A * | 9/1998 | Chan .............................. 204/418 |
| 5,846,708 | A | 12/1998 | Hollis et al. |
| 6,203,981 | B1 | 3/2001 | Ackley et al. |
| 6,946,675 | B2 | 9/2005 | Braun et al. |
| 6,967,363 | B1 * | 11/2005 | Buller ............................ 257/288 |
| 2004/0005572 | A1 | 1/2004 | Rosner et al. |
| 2004/0110277 | A1 | 6/2004 | Maeda |
| 2005/0106587 | A1 * | 5/2005 | Klapproth et al. ................. 435/6 |
| 2005/0123937 | A1 * | 6/2005 | Thorp et al. ...................... 435/6 |
| 2006/0001191 | A1 | 1/2006 | Cusson et al. |
| 2006/0011911 | A1 | 1/2006 | Bockelmann et al. |
| 2006/0141474 | A1 * | 6/2006 | Miyahara et al. ................. 435/6 |
| 2006/0223170 | A1 * | 10/2006 | Kamahori et al. ......... 435/287.2 |
| 2007/0235760 | A1 * | 10/2007 | Shim et al. .................... 257/192 |

OTHER PUBLICATIONS

Korean Office Action with English Translation for Application No. 10-2006-0032413 dated Mar. 23, 2012.

* cited by examiner

*Primary Examiner* — Marc Armand
(74) *Attorney, Agent, or Firm* — Cantor Colburn LLP (57) ABSTRACT

A field effect transistor for detecting an analyte having a thiol group includes a substrate, a source region and a drain region formed apart from each other on the substrate, the source region and the drain region being doped such that a polarity of the source and drain region is opposite to a polarity of the substrate, a channel region disposed between the source region and the drain region, an insulating layer formed of an electrically insulating material and disposed on the channel region, a gold layer disposed on the insulating layer and a reference electrode disposed apart from the gold layer.

16 Claims, 5 Drawing Sheets

FIELD EFFECT TRANSISTOR COMPRISING GOLD LAYER, MICROFLUIDIC DEVICE COMPRISING THE FIELD EFFECT TRANSISTOR, AND METHOD OF DETECTING ANALYTE HAVING THIOL GROUP USING THE FIELD EFFECT TRANSISTOR AND THE MICROFLUIDIC DEVICE

This application claims priority to Korean Patent Application No. 10-2006-0032413, filed on Apr. 10, 2006, and all the benefits accruing therefrom under 35 U.S.C. §119, the contents of which in its entirety are herein incorporated by reference.

BACKGROUND OF THE INVENTION

1. Field of the Invention

The present invention relates to a field effect transistor ("FET") having a gold layer, a microfluidic device including the FET and a method of detecting an analyte having a thiol group using the FET and the microfluidic device.

2. Description of the Related Art

A class of sensors for detecting biomolecules with electrical signals includes transistor-based biosensors having a structure including a transistor. These transistor-based biosensors are produced by applying the techniques of semiconductor processes, and are advantageous in terms of rapid conversion of electrical signals, easy integration of microelectromechanical systems ("MEMS") with integrated circuits and the like. Thus, considerable research has been conducted on these transistor-based biosensors in recent years.

The first patented invention to detect biological reactions using a field effect transistor ("FET") is disclosed in U.S. Pat. No. 4,238,757. The invention of the '757 patent relates to a biosensor for detecting an antigen-antibody reaction by measuring a current generated as a result of a change in a semiconductor inversion layer induced by a change in the surface charge concentration, and the biosensor is targeted to proteins among various biomolecules. U.S. Pat. No. 4,777,019 discloses a device for adsorbing a biological monomer on a surface of the gate of a FET, and measuring the extent of hybridization of a biological monomer with a complementary monomer using the FET.

U.S. Pat. No. 5,846,708 describes a method of determining whether a bound biomolecule is hybridized, by measuring the light absorption of the bound biomolecule using a charged coupled device ("CCD"). U.S. Pat. Nos. 5,466,348 and 6,203,981 describe methods of using a thin film transistor ("TFT") to enhance the signal-to-noise ratio by integrating the TFT with a circuit.

When a FET is used as a biosensor as described above, the FET is advantageously less expensive and detects biomolecules in less time than conventional methods. Furthermore, the FET used as the biosensor is easy to integrate into an integrated circuit ("IC")/MEMS process.

Figure 1A:
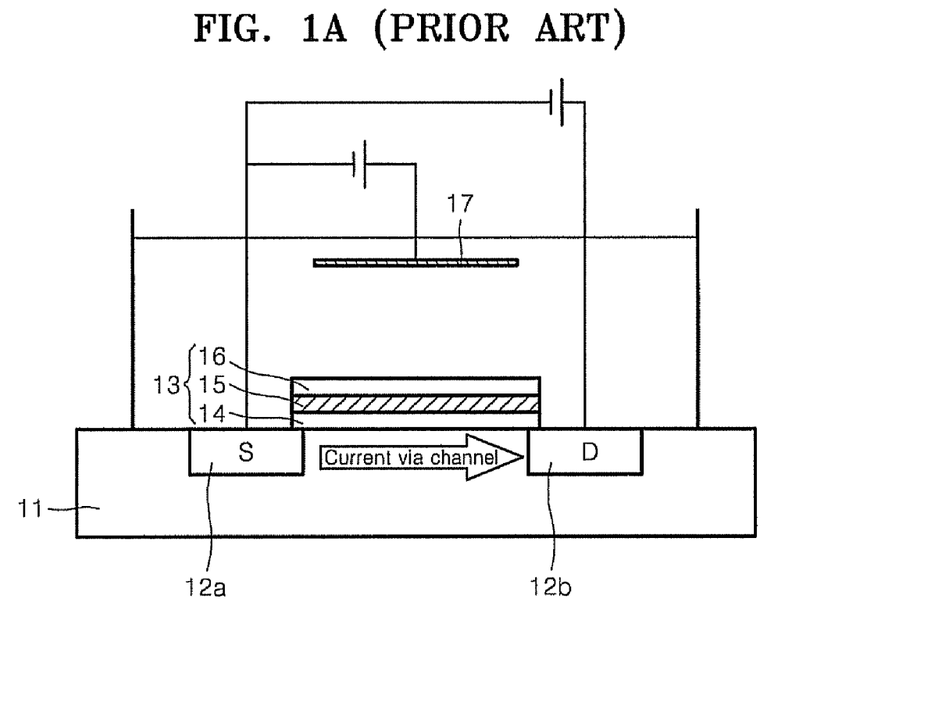
FIG. 1A is a diagram schematically illustrating the structure of a conventional field effect transistor ("FET") of the prior art.

The structure of a conventional FET is schematically illustrated in FIG. 1A. Referring to FIG. 1A, the FET includes a substrate 11 which is either doped with n-type or p-type impurities, a source 12a and a drain 12b which are formed apart from each other on two edges of the substrate 11 and a gate 13 which is formed on the substrate 11 to be in contact with the source 12a and the drain 12b. The source 12a and the drain 12b are doped to include a polarity opposite to that of the substrate 11. A channel is generally formed between the source 12a and the drain 12b. The gate 13 generally includes an oxide layer 14, a polysilicon layer 15 and a gate electrode layer 16, and probe biomolecules 18 are attached to the gate electrode layer 16. A reference electrode 17 is formed apart from the gate electrode. The probe biomolecules 18 bind with predetermined target biomolecules (not shown) by hydrogen bonding or the like, and this binding is electrically measured to determine the degree of binding between the probe biomolecules 18 and the target biomolecules.

Figure 1B:
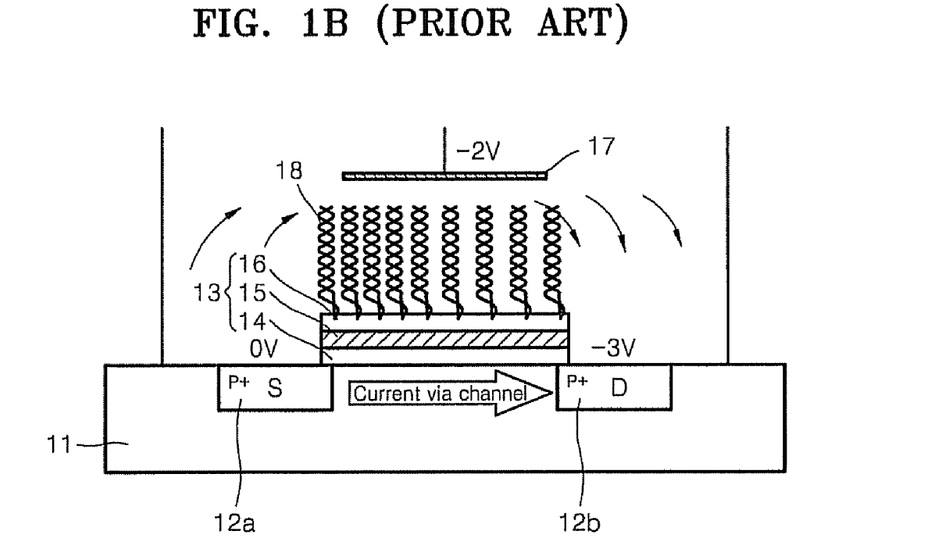
FIG. 1B is a diagram schematically illustrating the processes of immobilizing probe biomolecules onto the surface of a gate electrode layer, and allowing target biomolecules to bind to probe biomolecules in a conventional FET of the prior art.

FIG. 1B is a diagram schematically illustrating the process of immobilizing probe biomolecules 18 on the surface of the gate electrode layer 16, and allowing the probe biomolecules 18 to bind with the target biomolecules. Referring to FIG. 1B, an intensity of the current flowing through the channel may vary according to whether or not the probe biomolecules 18 are immobilized on the surface of the gate electrode layer 16, and also according to whether or not the target biomolecules bind with the immobilized probe biomolecules 18. Thereby, the target biomolecules can be detected by measuring the variance in the intensity of the current flowing through the channel. The conventional FETs as described above have a structure such that the probe biomolecules 18 are immobilized on a surface of the channel.

In conventional FETs, the current flowing through the channel of the FET is greatly affected by the ion concentration of an analyte, and sensitivity of the conventional FET is poor. The reason for the poor sensitivity of the FET is that an increase in ion concentration of the analyte causes masking of molecular charges and subsequent deterioration of the sensitivity of the FET for use as a sensor. U.S. Patent Application No. 2006001191 ("the 191 patent application") discloses a method of analyzing a polymerase chain reaction ("PCR") product by purifying the PCR product with a buffer, such as a 10 millimolar (mM) tris hydrochloride ("Tris-HCl") buffer, spotting the purified PCR product on a FET to which polylysine is immobilized, washing and electrically detecting the PCR product in a 0.01 mM potassium chloride ("KCl") solution. Thus, the method of the '191 patent application necessarily includes the process of washing. However, in the case of a lab-on-a-chip ("LOC"), the LOC is required to perform a series of processes on the same chip, including measurement, as well as collection, separation, amplification and purification of the sample to be analyzed, and solutions used in these serial processes typically have high ion concentrations.

BRIEF SUMMARY OF THE INVENTION

In an attempt to address the problems discussed above, such as that measurement is possible only at low ion concentrations, and the solutions for measurement need to be replaced, the inventors of the present invention conducted extensive research, and disclose herein a device and a method for detecting an analyte, based on the property that molecules having thiol groups spontaneously and rapidly bind to gold, according to exemplary embodiments of the present invention.

The present invention provides a field effect transistor ("FET") which can detect an analyte having a thiol group even at high ion concentrations, and a microfluidic device including the FET.

The present invention also provides a method of detecting an analyte having a thiol group with high sensitivity using the FET and the microfluidic device.

According to an exemplary embodiment of the present invention, there is provided a FET including a substrate, a source region and a drain region formed apart from each other on the substrate, the source region and the drain region doped such that a polarity of the source and drain region is opposite to a polarity of the substrate, a channel region disposed between the source region and the drain region, an insulating layer formed of an electrically insulating material disposed on the channel region, a gold layer disposed on the insulating layer and a reference electrode disposed apart from the gold layer.

According to an exemplary embodiment of the present invention, there is provided a microfluidic device including an inlet and an outlet, each in fluid communication with a microchannel, the microfluidic device including a FET, the FET including a substrate, a source region and a drain region formed apart from each other on the substrate and doped such that a polarity of the source and drain region is opposite to a polarity of the substrate, a channel region disposed between the source region and the drain region, an insulating layer formed of an electrically insulating material disposed on the channel region, a gold layer disposed on the insulating layer and a reference electrode disposed apart from the gold layer, wherein the FET is in fluid communication with the microchannel.

According to an exemplary embodiment of the present invention, there is provided a method of detecting an analyte having a thiol group using the FET including a substrate, a source region and a drain region formed apart from each other on the substrate, the source region and the drain region doped such that a polarity of the source and drain region is opposite to a polarity of the substrate, a channel region disposed between the source region and the drain region, an insulating layer formed of an electrically insulating material and disposed on the channel region, a gold layer disposed on the insulating layer and a reference electrode disposed apart from the gold layer, the method includes contacting a sample containing the analyte having a thiol group with the gold layer of the FET and measuring a current flowing through the channel region between the source region and the drain region of the FET.

According to an exemplary embodiment of the present invention, there is provided a method of detecting an analyte having a thiol group using the microfluidic device including an inlet and an outlet, each in fluid communication with a microchannel, the microfluidic device including a field effect transistor, the field effect transistor comprising a substrate, a source region and a drain region formed apart from each other on the substrate and doped such that a polarity of the source and drain region is opposite to a polarity of the substrate, a channel region disposed between the source region and the drain region, an insulating layer formed of an electrically insulating material and disposed on the channel region, a gold layer disposed on the insulating layer, and a reference electrode disposed apart from the gold layer, wherein the field effect transistor is in fluid communication with the microchannel, the method includes contacting a sample containing the analyte having a thiol group with the gold layer and measuring a current flowing through the channel region disposed between the source region.

BRIEF DESCRIPTION OF THE DRAWINGS

The above and other aspects, features and advantages of the present invention will become more apparent by describing in more detail exemplary embodiments thereof with reference to the accompanying drawings, in which.

DETAILED DESCRIPTION OF THE INVENTION

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

As used herein, the term "microfluidic device" incorporates the concept of a microfluidic device that comprises microfluidic elements such as, e.g., microfluidic channels (also called microchannels or microscale channels). As used herein, the term "microfluidic" refers to a device component, e.g., chamber, channel, reservoir, or the like, that includes at lest one cross-sectional dimension, such as depth, width, length, diameter, etc. of from about 0.1 micrometer to about 1000 micrometer. Thus, the term "microchamber" and "microchannel" refer to a channel and a chamber that includes at least one cross-sectional dimension, such as depth, width, and diameter of from about 0.1 micrometer to about 1000 micrometer, respectively.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will now be described in detail with reference to the accompanying drawings.

Figure 2:
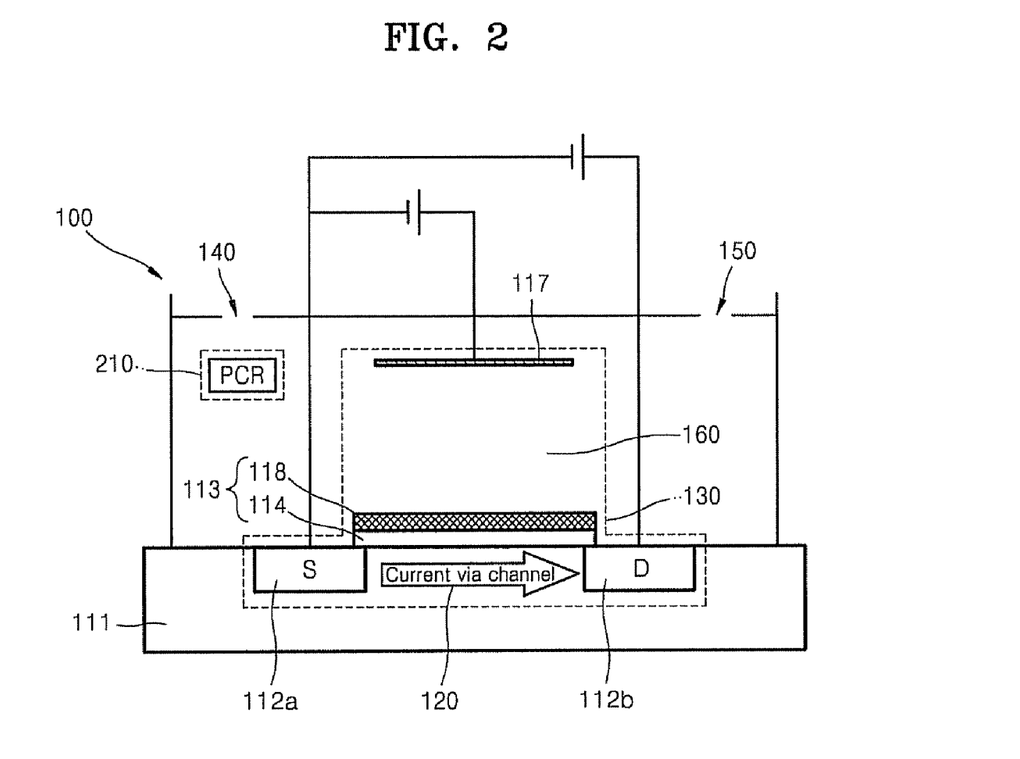
FIG. 2 is a diagram schematically illustrating a FET and a microfluidic device according to an exemplary embodiment of the present invention.

FIG. 2 is a diagram schematically illustrating a FET and a microfluidic device according to an exemplary embodiment of the present invention. Referring to FIG. 2, a field effect transistor ("FET") 130 for detecting an analyte having a thiol group includes a source region 112a and a drain region 112b which are formed apart from each other on a substrate 111, and the source and drain region 112a and 112b, respectively, are doped to include a polarity opposite to a polarity of the substrate 111. Still referring to FIG. 2, a channel region 120 is disposed between the source region 112a and the drain region 112b. A gate 113 which is formed on the substrate 111 to be in contact with the source 112a and the drain 112b includes an insulating layer 114, and a gold layer 118. The insulating layer 114, which is formed of an electrically insulating material, is disposed on the channel region 120. The gold layer 118 is disposed on the insulating layer 114 and a reference electrode 117 is disposed apart from the gold layer 118.

According to the current exemplary embodiment of the present invention, the semiconductor material of the substrate 111 is formed of silicon, while in alternative exemplary embodiments, the substrate 111 may include group III-V semiconductor materials or other semi-conductor materials with similar characteristics. The insulating layer 114 may be formed of a material selected from the group consisting of silicon dioxide and silicon nitride, however, the insulating layer 114 in the present invention is not limited to these materials.

In the field effect transistor 130 according to exemplary embodiments of the present invention, the substrate 111 may be doped with n-type impurities, while the source region 112a and the drain region 112b may be doped with p-type impurities. In alternative exemplary embodiments, the substrate 111 may be doped with p-type impurities, while the source region 112a and the drain 112b region may be doped with n-type materials.

FIG. 2 is a diagram schematically illustrating a microfluidic device 100 including a FET 130 according to an alternative exemplary embodiment of the present invention. Referring to FIG. 2, the microfluidic device 100 includes an inlet 140 and an outlet 150, each in fluid communication with a microchannel 160. The microfluidic device 100 includes the FET 130 according to an exemplary embodiment of the present invention, wherein the FET 130 is in fluid communication with the microchannel 160. In an alternative exemplary embodiment, the FET 130 is formed within the microchannel 160. The FET 130 includes a source region 112a and a drain region 112b which are formed apart from each other on the substrate 111, and the source and drain region 112a and 112b, respectively, are doped to include a polarity opposite to the polarity of the substrate 111. A channel region 120 is disposed between the source region 112a and the drain region 112b. A gate 113 which is formed on the substrate 111 to be in contact with the source 112a and the drain 112b includes an insulating layer 114, and a gold layer 118. The insulating layer 114, which is formed of an electrically insulating material, is disposed on the channel region 120. The gold layer 118 is disposed on the insulating layer 114 and the field effect transistor 130 is in fluid communication with the microchannel 160. A reference electrode 117 is disposed within the microfluidic device 100 apart from the gold layer 118 and electrically connected to the source region 112a and the drain region 112b according to an exemplary embodiment of the present invention.

According to the current exemplary embodiment of the present invention, the semiconductor material of the substrate 111 of the FET 130 in the microfluidic device 100 may be silicon, while the insulating layer 114 of the FET 130 in the microfluidic device 100 may be formed of a material selected from the group consisting of silicon dioxide and silicon nitride, however the present invention is not limited to these materials.

Figure 3:
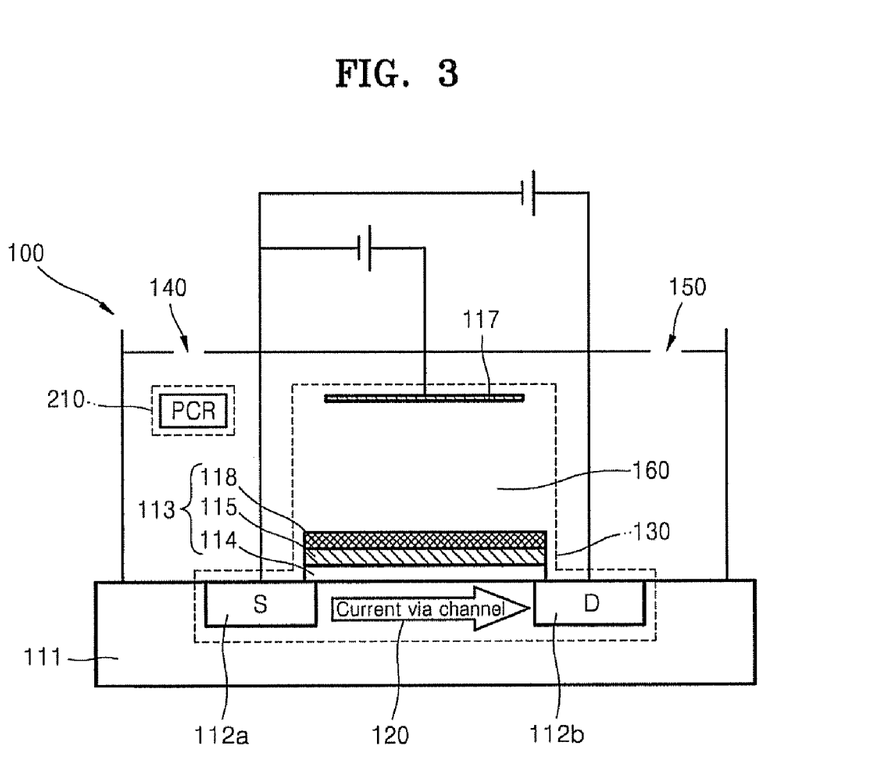
FIG. 3 is a diagram schematically illustrating a FET and a microfluidic device including a FET according to an alternative exemplary embodiment of the present invention.

FIG. 3 is a diagram schematically illustrating a FET and a microfluidic device including a FET according to an alternative exemplary embodiment of the present invention. Referring to FIG. 3, according to another exemplary embodiment of the present invention, the FET 130 in the microfluidic device 200 may further comprise a polysilicon layer 115 disposed between the insulating layer 114 and the gold layer 118.

In the microfluidic device 200 according to the current exemplary embodiment of the present invention, the substrate 111 of the FET 130 may be doped with n-type impurities, while the source region 112a and the drain region 112b of the FET 130 may be doped with p-type impurities. In alternative exemplary embodiments, the substrate 111 may be doped with p-type impurities, while the source region 112a and the drain region 112b may be doped with n-type materials.

According to another exemplary embodiment of the present invention, the substrate 111 of the FET 130 in the microfluidic device 100 may form the internal wall of the microchannel 160, which is in turn formed of a semiconductor material. In alternative exemplary embodiments, the substrate 111 may form a part or the entirety of the internal wall of the microchannel 160.

According to another exemplary embodiment of the present invention, the microfluidic device 100 may comprise a polymerase chain reaction ("PCR") amplification unit 210 disposed inside the microchannel 160 or disposed in fluid communication with the microchannel 160. In an exemplary embodiment, the PCR amplification unit 210 may be disposed between the inlet and the FET 130. The PCR amplification unit 210 is an apparatus including a heater (not shown), a cooler (not shown) and a reaction chamber (not shown), wherein the temperature of a reaction solution is controlled by thermal cycling such that a nucleic acid in the reaction solution can be amplified by a polymerization reaction. The PCR amplification unit 210 is well known to one of having ordinary skill in the art, and the microfluidic device 100 according to exemplary embodiments of the present invention includes such a conventionally known PCR amplification unit 210.

In an exemplary embodiment of the present invention, a method of detecting an analyte including a thiol group using a FET 130 according to the present invention is provided. The exemplary method includes contacting a sample containing the analyte including a thiol group with the gold layer 118 of the FET 130, and measuring the current flow through the channel region 120 between the source region 112a and the drain region 112b of the FET 130.

According to the current exemplary embodiment, the analyte may be any biomolecule containing a thiol group. Exemplary embodiments of the analyte may include proteins, nucleic acids and sugars, which respectively include thiol groups. In alternative exemplary embodiments, the analyte may be a nucleic acid labeled with a thiol group at either the 3' terminal or the 5' terminal, or a thiol group labeled at both the 3' terminal and the 5' terminal. In an exemplary embodiment of the analyte, nucleic acid which includes pure nucleic acid, as well as a PCR product and a nucleic acid purification product which is eluted using a commercially available kit (e.g., Qiagen® nucleic acid purification kit) is used as the analyte. The nucleic acid purification kit may contain a chaotropic agent such as guanidine hydrochloride ("GuHCl"). The measurement of current is performed by applying a voltage to the gold layer 118 via the reference electrode 117, and measuring the current flowing through the channel region 120 between the source region 112a and the drain region 112b.

According to another exemplary embodiment of the present invention, a method of detecting an analyte having a thiol group using a microfluidic device 100 according to an exemplary embodiment of the present invention is provided, the method includes contacting a sample containing the analyte having a thiol group with the gold layer 118 of the FET 130 in the microfluidic device 100, and measuring the current flowing through the source region 112a and the drain region 112b of the FET 130.

According to the current exemplary embodiment of the present invention, the analyte may be any biomolecule containing a thiol group. Exemplary embodiments of the analyte include proteins, nucleic acids and sugars, which respectively include thiol groups. Exemplary embodiments of the analyte may include a nucleic acid labeled with a thiol group at either the 3' terminal or the 5' terminal, or a thiol group labeled at both the 3' terminal and the 5' terminal. In alternative exemplary embodiments, the nucleic acid as the analyte includes pure nucleic acid, as well as a PCR product and a nucleic acid purification product which has been eluted using a commercially available kit (e.g., Qiagen® nucleic acid purification kit). The nucleic acid purification kit may contain a chaotropic agent such as GuHCl. The measurement of current is performed by applying a voltage to the gold layer 118 via the reference electrode 117, and measuring the current flowing through the channel region 120 between the source region 112a and the drain region 112b.

In the methods according to exemplary embodiments of the present invention, when the analyte having a thiol group in the sample is contacted with the gold layer 118 present in the channel region 120 (hereinafter, may be referred to as "gate region") of the FET 130, the thiol group spontaneously and rapidly binds to the gold layer 118. This binding induces changes in the electrical signals such as voltage and current flowing through the channel region 120 of the FET 130, and measuring these changes in the electrical signals allows for the detection of the analyte in the sample.

The methods according to exemplary embodiments of the present invention allow detection of an analyte having a thiol group with high sensitivity at high ion concentrations, for example, even at an ion concentration of 60 mM or higher. Furthermore, since the analyte can be directly detected without undergoing a washing process after the process of spotting the analyte on the surface of the gate of the FET 130, the exemplary methods of the present invention allow for the reduction in the size of devices for biomolecule detection, and can be easily applied to lab-on-a-chip technology.

Hereinafter, the present invention will be described in more detail with reference to the following examples. However, these examples are for illustrative purposes only and are not intended to limit the scope of the present invention by any means.

EXAMPLES

Comparative Example 1

Effect of Ion Concentration on the Current Flowing Through the Channel of Conventional FET The FET element used in the current example was produced to order by X-FAB Semiconductor Foundries AG in Germany. This custom-produced product contained 192 FETs including an identical structure and electrical characteristics. The 192 FETs were arranged in an array (12 FETs× 16 rows) on a substrate. The FET element was produced using the facilities of X-FAB Semiconductor Foundries, using a complementary metal oxide semiconductor ("CMOS") manufacturing process exclusive to the company. CMOS manufacturing processes may slightly vary from company to company, but the process itself is not a factor having a large influence on the characteristics of FET elements. Since the CMOS manufacturing process is irrelevant to the scope of the present invention, a description thereof will not be provided here. Each of FET element used in this Example 1 has the structure as described in FIG. 1A, that is, the FET includes a silicon wafer 11 which is doped with Ga, a source 12a and a drain 12b which are formed apart from each other on two edges of the silicon wafer 11 and a gate 13 which is formed on the silicon wafer 11 to be in contact with the source 12a and the drain 12b. The source 12a and the drain 12b are doped with P to include a polarity opposite to that of the silicon wafer 11. A channel is formed between the source 12a and the drain 12b. The gate 13 includes an silicon oxide layer 14, a polysilicon layer 15 and a gate electrode layer 16. The gate electrode layer is made of silicon oxide.

A FET-based sensor for detecting ionic substances, comprising two chambers, including a sensing chamber and a reference chamber, was produced by installing sidewalls on the array substrate, and installing an upper substrate coated with platinum as a reference electrode on the surface thereof.

In the current example, an eluate was obtained by performing purification without deoxyribonucleic acid ("DNA") using a commercially available Qiagene kit (QIAquick® PCR Purification Kit), and the obtained eluate was injected into the FET-based sensor. A voltage was applied to the gate electrode via the reference electrode 17, and the current flowing through the channel region between the source region and the drain region was measured.

The procedure for performing purification without DNA is as follows. First, 250 µl of a binding buffer (PB buffer, QIAquick®) was injected into a purification tube of the Qiagen® kit, and then was aspirated by a vacuum for 10 to 30 seconds. Next, 750 µl of a washing buffer (PE buffer, QIAquick®) was injected into the purification tube, and then was aspirated by a vacuum for 10 to 30 seconds. The purification tube was centrifuged at 13,000 revolutions per minute (rpm) for 1 minute. After completing the washing process, 30 µl of distilled water was injected into the purification tube, and the purification tube was incubated for 1 minute and then subjected to centrifugation at 13,000 rpm for 1 minute. Thus, 25 to 30 µl of an eluate was obtained at the bottom of the purification tube.

For the measurement of electric current using the FET-based sensor, a sample was passed through the FET-based sensor at a flow rate of 0.5 µl/min, and a direct current (DC) voltage of 3.3 V was applied to the gate electrode via the reference electrode 17. Then the current flowing through the channel region between the source region and the drain region was measured.

As a result, when the distilled water eluate was injected into the FET-based sensor, the current increased. The FET used in this example was of negative-channel metal-oxide semiconductor ("NMOS") type, in which the current is decreased when DNA is brought into contact with the channel. The distilled water eluate showed a signal pattern which contradicted the signal pattern which can be usually seen with DNA is brought into contact with the channel. It is believed that the presence of a chaotropic agent such as guanidine hydrochloride ("GuHCl") in the distilled water eluate had an influence on the current flowing through the FET.

Figure 4:
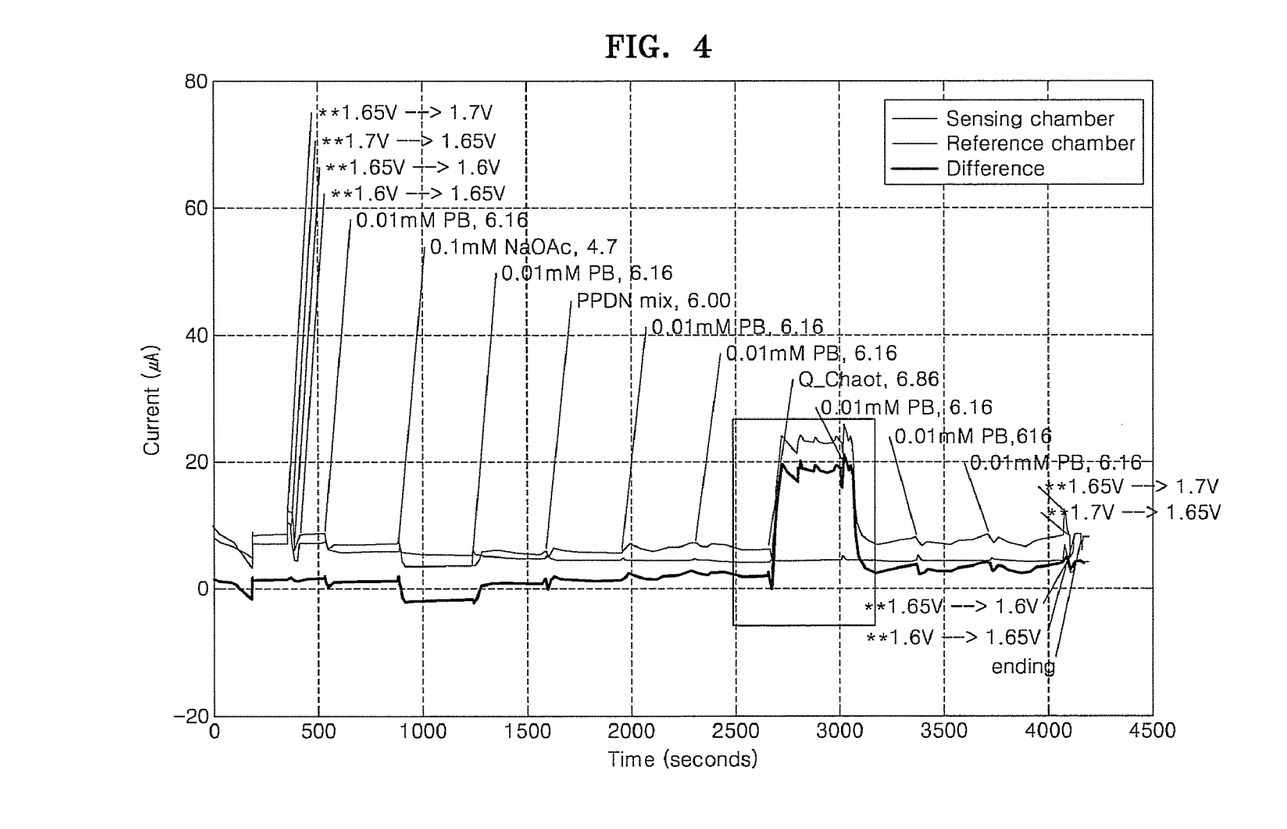
FIG. 4 is a graph showing changes in the current flowing through the channel region in a FET used in the Example 1, when a 0.01 mM phosphate buffer (PB; pH 6.0), a 0.1 mM sodium acetate (NaOAc buffer; pH 4.7) and a distilled water eluate of a Qiagen® kit were passed through the channel region.

FIG. 4 is a graph showing changes in the current flowing through the channel region in a FET according to the present Example, when a 0.01 mM phosphate buffer (PB; pH 6.0), a 0.1 mM NaOAc buffer (pH 4.7), and a distilled water eluate of a Qiagen® kit were allowed to flow through the channel region. Referring to FIG. 1A, when the NaOAc buffer, which has the same negative charge as that of DNA, flowed through the channel region, the current in the channel region of the FET was decreased. However, when the distilled water eluate flowed through the channel region, the current was increased.

Therefore, a FET element which can generate current in the channel region and allows detection of an analyte even at high ion concentrations is desired.

Example 1

Production of FET-Based Biosensor

The FET element used in this example was produced using the facilities of X-FAB Semiconductor Foundries AG in Germany, using the KC10-1.0 µm CMOS manufacturing process of the company. The produced FET element was of NMOS type. The produced FET element had 192 FETs including an identical structure and electrical characteristics, which were arranged in an array (12 FETs×16 rows) on a substrate. CMOS manufacturing processes may vary slightly from company to company, however the process itself is not a factor having a large influence on the characteristics of FET elements. Since the CMOS manufacturing process used by the company is irrelevant to the scope of the present invention, a description thereof will not be provided here. Each of the FET element used in this example has the same structure that of used in Comparative example 1 except that the polysilicon layer 15 and the gate electrode layer 16 has been replaced with a gold layer 118.

First, a passivation layer (nitride layer) of the FET element was removed, and the gate region (silicon oxide) was exposed to the outside. The CMOS manufacturing process was conducted by X-FAB Semiconductor Foundries, but the subsequent processes, which are related to the present invention, were performed by the inventors themselves. Next, the surface of the FET element including the exposed gate region was carefully washed with pure acetone and water, and then dried. This substrate washing process was performed using a wet station which is commonly used in semiconductor production processes. After completing the washing process, the FET element was dried by spin drying.

Gold (Au) was deposited on the surface of the gate region of the FET element. The deposition was performed using a lift-off process. Patterning was performed on the gate region using an AZ5214® photosensitive film. A titanium (Ti) layer was deposited to a thickness of 50 nanometer (nm), and then a gold (Au) layer was deposited to a thickness of 500 nm on the silicon oxide layer of the gate region. Patterning with gold was performed only on the upper face of the gate region using the lift-off process.

Next, an FET-based sensor for detecting ionic substances, comprising two chambers, including a sensing chamber and a reference chamber, was produced by installing sidewalls on the array substrate, which included the FET element containing 192 gold-layered surfaces produced as described above, and installing an upper substrate coated with platinum as a reference electrode on the surface thereof.

Example 2

Detection of PCR Product Labeled with Thiol Group, Using FET

<1. Detection of PCR Product Labeled with Thiol Group>
DNA amplification was performed by PCR, using the genome of *Staphylococcus aureus* as the template, and using a forward primer (5'-HS-(CH$_2$)$_6$-TAG CAT ATC AGA AGG CAC ACC C-3': SEQ ID NO: 1) and a reverse primer (5'-HS- (CH$_2$)$_6$-ATC CAC ATC AGA GAG ACA AC ATT-3': SEQ ID NO:2). Since the obtained PCR product, including the amplification product as well as the residual primers, included thiol groups, thus being reactive with gold (Au) on the FET element, the PCR product was subjected to purification. The purification was performed in the same manner as in Comparative Example 1. 250 μl of a binding buffer (PB buffer, QIAquick®) and 50 microliter (μl) of the PCR product were mixed, and the resulting mixture was injected into a purification tube of a Qiagene kit, which was then aspirated by a vacuum for 10 to 30 seconds. Next, 750 μl of a washing buffer (PE buffer, QIAquick®) was injected into the purification tube, which was then aspirated by a vacuum for 10 to 30 seconds. The purification tube was centrifuged at 13,000 rpm for 1 minute. After completing the washing process, 30 μl of distilled water was injected into the purification tube, and the purification tube was left to stand for 1 minute and then centrifuged at 13,000 rpm for 1 minute. 25 to 30 μl of an eluate was obtained at the bottom of the purification tube. The obtained eluate was quantified, and then the concentration of the eluate was adjusted. The concentration of the PCR amplification product to be injected in the test for FET element was 9 nanogram/microliter (ng/μl), and the PCR amplification product was diluted using a 150 mM Phosphate Buffered Saline (PBS; pH 7.4) solution.

The FET element produced in Example 1 as described above was connected to a current-measuring device manufactured by the inventors, and then a 150 mM PBS (pH 7.4) was passed through the FET element at a flow rate of 0.5 μl/min. A direct current (DC) voltage of 3.3 V was applied to the gold layer 118 via the reference electrode 117, and the current in the channel region between the source region and the drain region was measured. The overall test procedure was conducted in two separate modes, namely, a sensing experiment mode and a reference experiment mode. The sensing experiment was an experiment for a sample with which an actual reaction took place, while the reference experiment was an experiment performed using a 150 mM PBS (pH 7.4) for noise compensation for all tests. Such division of the test procedure into two experiment modes was for the compensation of signal drift, and the difference obtained from the value obtained from the sensing experiment minus the value obtained from the reference experiment, was taken as the actual signal value. When the FET element was stabilized, the purified PCR amplification product was injected into the FET element.

Figure 5:
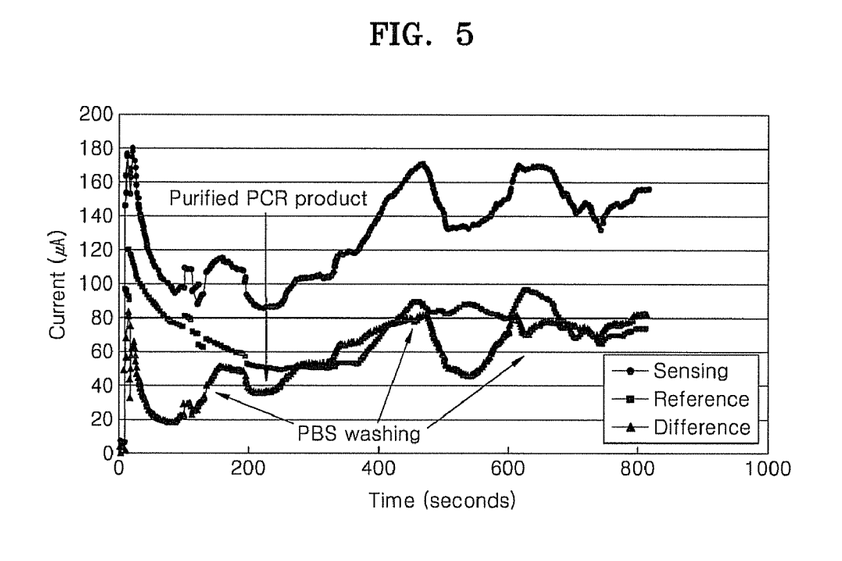
FIG. 5 is a graph showing the results of measuring changes in the current, after allowing a purified polymerase chain reaction ("PCR") amplification product to flow through a FET according to an exemplary embodiment of the present invention.

FIG. 5 is a graph showing the results of measuring changes in the current obtained after passing a purified PCR amplification product through a FET according to an exemplary embodiment of the present invention. When the FET element was stabilized, it was initially confirmed that no influence was exerted by a 150 mM PBS solution when allowed to flow through the FET element, and then the purified PCR amplification product was injected into the FET element. As shown in FIG. 5, the amount of current flow increased when the purified PCR amplification product was injected. It is thought to be because the thiol groups present in the PCR amplification product reacted with the gold coated on the surface of the FET element and changed the electrical properties of the FET element. The current increased by approximately 25 to 30 micro amperes (μA). The current also temporarily decreased after washing with a 150 mM PBS solution and then returned to its original value.

<2. Negative Control Test>

It was confirmed in "1. Detection of PCR product labeled with thiol group" that a purified PCR product could be detected using the FET according to an exemplary embodiment of the present invention. In this section, the effect of the PCR solution on the method of detecting using the FET according to an exemplary embodiment of the present invention was examined.

First, as a negative control test, a PCR reaction and a purification process were performed in the same manner as in Section 1, except that no template was used during the PCR reaction. Thus, a purification product of PCR product at pH 7.47 (referred to as a "negative control solution") was obtained.

The FET element produced in Example 1 was connected to a current measuring device manufactured by the inventors, and a 150 mM PBS solution was injected into the FET element. When the FET element was stabilized, the purification product obtained as above was injected into the FET element.

Figure 6:
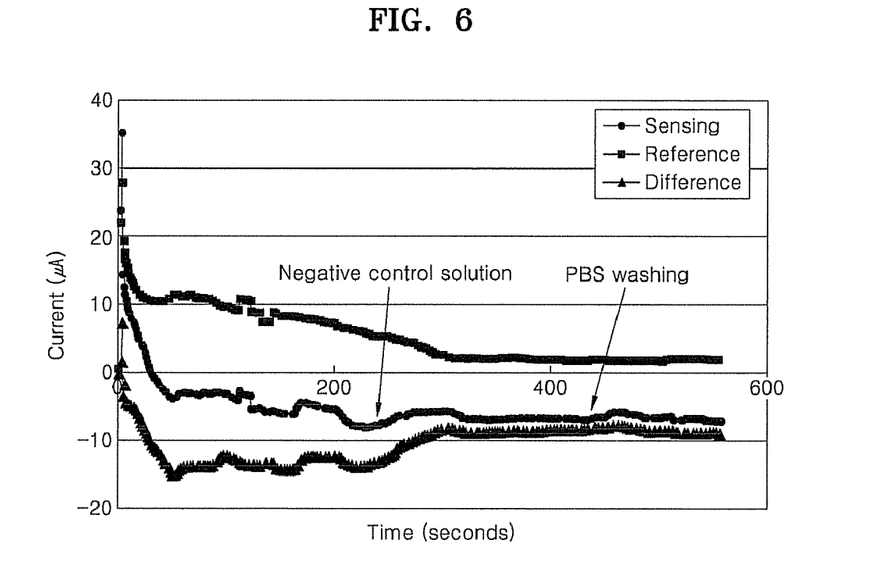
FIG. 6 is a graph showing changes in the current in a negative control test using a FET according to an exemplary embodiment of the present invention, in which a PCR reaction is performed using a PCR solution containing no template to obtain a PCR product, the PCR product is purified and the purified PCR product is injected into the FET.

FIG. 6 is a graph showing changes in the current in a negative control test using a FET according to an exemplary embodiment of the present invention. In the test, a PCR reaction was performed using a PCR solution containing no template to obtain a PCR product, the PCR product was purified, and the purified PCR product was injected into the FET. When the FET element was stabilized, a 150 mM PBS solution was first passed through the FET element to confirm that the PBS solution had no effect on the current, and then the negative control solution was injected into the FET element. The amount of current flow slightly increased after the negative control solution was injected, however the degree of increase was much smaller compared with the amount of increase of current flow that was observed in the Detection of PCR product labeled with thiol group example. The current increased by approximately 5 μA, and this small increase can be interpreted to be due to the influence of unpurified primers.

The FET according to the present invention can be used for electrically detecting an analyte having a thiol group even at high ion concentrations.

The microfluidic device according to the present invention can be used for electrically detecting an analyte having a thiol group even at high ion concentrations.

The method of detecting an analyte using the FET or microfluidic device according to the present invention allows for detection of an analyte with high sensitivity even at high ion concentrations.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A field effect transistor comprising:
a substrate;
a source region and a drain region disposed apart from each other on the substrate, the source region and the drain region doped such that a polarity of the source and drain region is opposite to a polarity of the substrate;
a channel region disposed between the source region and the drain region;
an insulating layer comprising an electrically insulating material and disposed on the channel region;
a gold layer disposed on the insulating layer, wherein probe biomolecules are not immobilized on a surface of the gold layer; and
a reference electrode disposed apart from the gold layer, wherein the gold layer is in fluid communication with the reference electrode.

2. The field effect transistor of claim 1, wherein the substrate comprises a semiconductor material.

3. The field effect transistor of claim 1, further comprising a polysilicon layer disposed between the insulating layer and the gold layer.

4. The field effect transistor of claim 1, further comprising a polymerase chain reaction amplification unit in fluid communication with the gold layer.

5. The field effect transistor of claim 2, wherein the semiconductor material is silicon, and the insulating layer comprises a material selected from the group consisting of silicon dioxide and silicon nitride.

6. A microfluidic device including an inlet and an outlet, each in fluid communication with a microchannel, the microfluidic device comprising a field effect transistor, the field effect transistor comprising:
a substrate;
a source region and a drain region disposed apart from each other on the substrate, the source region and the drain region doped such that a polarity of the source and drain regions is opposite to a polarity of the substrate;
a channel region disposed between the source region and the drain region; an insulating layer comprising an electrically insulating material and disposed on the channel region;
a gold layer disposed on the insulating layer, wherein probe biomolecules are not immobilized on a surface of the gold layer; and
a reference electrode disposed apart from the gold layer, wherein the gold layer is in fluid communication with the reference electrode, wherein the field effect transistor is in fluid communication with the microchannel.

7. The microfluidic device of claim 6, wherein the substrate is formed of a semiconductor material.

8. The microfluidic device of claim 6, wherein the field effect transistor further comprises a polysilicon layer disposed between the insulating layer and the gold layer.

9. The microfluidic device of claim 6, wherein the microchannel comprises a PCR amplification unit disposed between the inlet and the field effect transistor.

10. The microfluidic device of claim 7, wherein the semiconductor material of the field effect transistor is silicon, while the insulation layer of the field effect transistor is formed of a material selected from the group consisting of silicon dioxide and silicon nitride.

11. A method of detecting an analyte having a thiol group using a field effect transistor comprising a substrate, a source region and a drain region disposed apart from each other on the substrate, the source region and the drain region doped such that a polarity of the source and drain region is opposite to a polarity of the substrate, a channel region disposed between the source region and the drain region, an insulating layer comprising an electrically insulating material and disposed on the channel region, a gold layer disposed on the insulating layer, wherein the probe biomolecules are not immobilized on a surface of the gold layer, and a reference electrode disposed apart from the gold layer, the method comprising:
contacting a sample containing an analyte having a thiol group with the gold layer of the field effect transistor; and
measuring a current flowing through the channel region between the source region and the drain region of the field effect transistor.

12. The method of claim 11, wherein the analyte is a nucleic acid labeled with a thiol group selected from the group consisting of the nucleic acid labeled with the thiol group at a 3' terminal, at a 5' terminal and at both the 3' terminal and the 5' terminal.

13. The method of claim 12, wherein the nucleic acid includes a polymerase chain reaction product and a purification product of the polymerase chain reaction.

14. A method of detecting an analyte having a thiol group using a microfluidic device including an inlet and an outlet, each in fluid communication with a microchannel, the microfluidic device comprising a field effect transistor, the field effect transistor comprising a substrate, a source region and a drain region disposed apart from each other on the substrate, the source region and the drain region doped such that a polarity of the source and drain region is opposite to a polarity of the substrate, a channel region disposed between the source region and the drain region, an insulating layer comprising an electrically insulating material and disposed on the channel region, a gold layer disposed on the insulating layer, wherein probe biomolecules are not immobilized on a surface of the gold layer, and a reference electrode disposed apart from the gold layer, wherein the gold layer is in fluid communication with the reference electrode, wherein the field effect transistor is in fluid communication with the microchannel, the method comprising:

contacting a sample containing the analyte having a thiol group with the gold layer; and measuring a current flowing through the channel region between the source region and the drain region.

15. The method of claim 14, wherein the analyte is a nucleic acid labeled with a thiol group selected from the group consisting of the nucleic acid labeled with the thiol group at a 3' terminal, a 5' terminal and at both the 3' terminal and the 5' terminal.

16. The method of claim 15, wherein the nucleic acid is a polymerase chain reaction product or a purification pro duct of the polymerase chain reaction.

* * * * *

SEQUENCE LISTING

<160> NUMBER OF SEQ ID NOS: 2

<210> SEQ ID NO 1
<211> LENGTH: 22

-continued

```
<212> TYPE: DNA
<213> ORGANISM: Artificial Sequence
<220> FEATURE:
<223> OTHER INFORMATION: Forward primer coupled with -(CH2)6SH at its 5
      terminal

<400> SEQUENCE: 1
tagcatatca gaaggcacac cc                                                 22

<210> SEQ ID NO 2
<211> LENGTH: 23
<212> TYPE: DNA
<213> ORGANISM: Artificial Sequence
<220> FEATURE:
<223> OTHER INFORMATION: Reverse primer coupled with -(CH2)6SH at its 5
      terminal

<400> SEQUENCE: 2
atccactcaa gagagacaac att                                                23
```